US 9,857,343 B2

(12) United States Patent
Yonezu et al.

(10) Patent No.: US 9,857,343 B2
(45) Date of Patent: Jan. 2, 2018

(54) GAS SENSOR WITH A RIBBED PROTECTIVE COVER

(71) Applicant: NGK Spark Plug Co., LTD., Nagoya (JP)

(72) Inventors: Kunihiko Yonezu, Inuyama (JP); Takehiro Oba, Kounan (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 7 days.

(21) Appl. No.: 14/990,605

(22) Filed: Jan. 7, 2016

(65) Prior Publication Data

US 2016/0223504 A1 Aug. 4, 2016

(30) Foreign Application Priority Data

Jan. 30, 2015 (JP) ................... 2015-016271
Nov. 13, 2015 (JP) ................... 2015-223121

(51) Int. Cl.
| | | |
|---|---|---|
| *G01N 33/00* | (2006.01) | |
| *G01N 27/406* | (2006.01) | |
| *G01N 27/407* | (2006.01) | |
| *G01M 15/10* | (2006.01) | |

(52) U.S. Cl.
CPC ...... *G01N 33/0009* (2013.01); *G01M 15/102* (2013.01); *G01N 27/4062* (2013.01); *G01N 27/4077* (2013.01); *G01N 27/4078* (2013.01)

(58) Field of Classification Search
CPC ............ G01M 15/102; G01N 33/0009; G01N 27/4077; G01N 27/4062; G01N 27/4078
See application file for complete search history.

(56) References Cited

U.S. PATENT DOCUMENTS

| | | | | |
|---|---|---|---|---|
| 4,169,388 A | * | 10/1979 | Teitelbaum | ............. G01L 23/22 73/114.21 |
| 4,269,685 A | * | 5/1981 | Parker | ................ A61B 5/14542 204/414 |
| 4,326,639 A | * | 4/1982 | Stahl | .................. B65D 41/3409 215/252 |
| 5,657,895 A | * | 8/1997 | Rogge | ................ B65D 51/1627 215/307 |

(Continued)

FOREIGN PATENT DOCUMENTS

JP 2012-251852 A 12/2012

*Primary Examiner* — Lisa Caputo
*Assistant Examiner* — Punam Roy
(74) *Attorney, Agent, or Firm* — Leason Ellis LLP

(57) ABSTRACT

A gas sensor includes a protective cover having a resin cylindrical cover portion at a rear end thereof, that can be airtightly attached to an attachment hole, and that can prevent a decrease in quality and a molding defect. A plurality of vertical ribs, which extend substantially parallel to an axis of a cylindrical cover portion, are formed on an outer peripheral surface of the cylindrical cover portion so that protrusions and recesses are provided in a circumferential direction. Due to the presence of the vertical ribs, as compared with an existing cylindrical cover portion that has a smooth outer peripheral surface without the vertical ribs, defects of the outer peripheral surface are not likely to occur in a molding process. Moreover, because slipping is not likely to occur when an operator holds and twists the cylindrical cover portion with his/her fingers, an attachment operation can be smoothly performed.

9 Claims, 10 Drawing Sheets

(56) References Cited

U.S. PATENT DOCUMENTS

| | | | | |
|---|---|---|---|---|
| D467,803 S | * | 12/2002 | Brown | D9/435 |
| D600,546 S | * | 9/2009 | Scilingo | D8/397 |
| D662,869 S | * | 7/2012 | Ballard | D12/213 |
| 8,657,140 B2 | * | 2/2014 | Iwami | B60K 15/0406 220/203.01 |
| D702,543 S | * | 4/2014 | Bell | D8/397 |
| 2004/0074284 A1 | * | 4/2004 | Day | G01N 27/407 73/23.31 |
| 2010/0170794 A1 | * | 7/2010 | Gibson | G01N 27/4062 204/406 |
| 2011/0174617 A1 | * | 7/2011 | Tsuzuki | G01N 27/407 204/431 |
| 2011/0259084 A1 | * | 10/2011 | Atsumi | G01N 27/4067 73/31.05 |
| 2014/0020446 A1 | * | 1/2014 | Yonezu | G01N 27/4062 73/23.2 |
| 2016/0223505 A1 | * | 8/2016 | Yonezu | G01N 33/0009 |

* cited by examiner

GAS SENSOR WITH A RIBBED PROTECTIVE COVER

This application claims the benefit of Japanese Patent Applications No. 2015-016271, filed Jan. 30, 2015 and No. 2015-223121, filed Nov. 13, 2015, which are incorporated herein by reference in their entity.

BACKGROUND OF THE INVENTION

1. Field of the Invention

The present invention relates to a gas sensor that is attached to an intake system (intake pipe or the like) or an exhaust system (exhaust pipe or the like) of an internal combustion engine, such as a diesel engine or a gasoline engine, and that is used to detect the concentration of a specific gas in a gas to be measured (detected), such as an intake gas or an exhaust gas.

2. Description of the Related Art

Gas sensors of this type include a detection element (also referred to as an "element") having a strip-like shape or a bar-like shape (shaft-like shape). A front end portion of the element serves as a detection portion, and a pair of electrodes (detection electrodes) are disposed on the front end portion. Examples of such gas sensors include a gas sensor (also referred to as a "sensor") that includes a metal shell, which has a tubular shape so that the gas sensor can be attached to a predetermined portion (attachment hole) of an object, such as an intake pipe or an exhaust pipe of an engine. The element of the sensor extends through the inside of the metal shell in the front-rear direction and fixed in position so that the detection portion protrudes from the front end of the metal shell. The sensor is airtightly attached to an attachment hole of an object so that the front end of the element is exposed to a gas to be detected and the element generates an electric signal in accordance with a gas concentration difference. The electric signal is output through electrode terminals, which are disposed on a portion of the element adjacent to a rear end of the element, to an engine controller unit (ECU), which is disposed outside the sensor, and is used to control the air-fuel ratio and the like.

Examples of means for attaching the gas sensor to the attachment hole and means for airtightly attaching the gas sensor include the following. One example is a method of screwing a metal shell, which has a threaded outer peripheral surface, into a threaded hole in the object. Another example is a press-fitting method in which an elastic sealing member, such as a ring-shaped rubber packing, is fitted and mounted into a groove formed in the outer peripheral surface of the metal shell, and the metal shell is press-fitted (pressed) into the attachment hole against a force generated by elastic deformation of the elastic sealing member (rubber packing) (Japanese Unexamined Patent Application Publication No. 2012-251852). With the press-fitting method, the rubber packing is compressively deformed between the inner peripheral surface of the attachment hole and the outer peripheral surface of the metal shell, and a gap between the inner and outer peripheral surfaces is airtightly sealed by using an elastic force generated due to the deformation. With this method, the sensor can be attached easily and rapidly by only pressing the sensor into the attachment hole in the axial direction. Therefore, this method is suitable for a case where the sensor is not used under severe conditions, such as a case where the gas pressure is low.

The gas sensor described in Japanese Unexamined Patent Application Publication No. 2012-251852 includes a resin protective cover (resin outer tube or the like) that is integrated with a rear portion of the metal shell by injection molding or the like, so that the structure of the gas sensor can be simplified. The protective cover accommodates and covers the rear end of the element, lead wires that are electrically connected to the element, connectors (metal terminals), and the like. The injection molding is performed, for example, by using a part (rear portion) of the metal shell as an insert (a component to be integrally embedded in a resin). The resin protective cover includes a cylindrical cover portion, which has a cylindrical shape substantially coaxial with the metal shell. The cylindrical cover portion covers the rear end of the detection element, which protrudes rearward from the metal shell, and metal terminals that are electrically connected to the element. An operator holds the cylindrical cover portion with his/her fingers when attaching the sensor to an attachment hole by using the press-fitting method. In the present application, the term "grip" may be used instead of "hold", and a portion to be gripped may be referred to as a "grip".

When attaching the sensor described in Japanese Unexamined Patent Application Publication No. 2012-251852 to an attachment hole by using the press-fitting method, it is necessary to press the sensor against an elastic force generated due to deformation of the rubber packing. Accordingly, in this operation, it is not possible to appropriately and smoothly attach the sensor by simply pressing the sensor straightly because the rubber packing (also referred to as the "rubber") becomes deformed or twisted. Therefore, when press-fitting the gas sensor, usually, the gas sensor is twisted by an appropriate angle in one direction or twisted (alternately) leftward and rightward by, for example, about 90 degrees.

However, fingers of an operator tend to slip over the cylindrical cover portion (grip) of the protective cover of the existing gas sensor described above, because the cover portion is made of a resin and has a cylindrical outer peripheral surface. Moreover, the existing gas sensor has a problem in that, although it is necessary to twist the gas sensor when press-fitting the gas sensor, it is not easy to twist the gas sensor appropriately against deformation of the rubber. Therefore, it has been pointed out that the operation of attaching the gas sensor by using the press-fitting method, which is expected to be easy, cannot be performed easily and rapidly. However, using a dedicated gripping tool to prevent slipping would increase the number of operation steps.

In addition to such a problem about the attachment operation, the existing gas sensor has the following problem. The cylindrical cover portion (grip) of the protective cover of the gas sensor is made of a resin and has a simply cylindrical outer peripheral surface and the outer peripheral surface is smooth (flat). Therefore, in a molding process, the outer peripheral surface (having a cylindrical shape) is likely to be deformed due to, for example, difference in contraction that occurs when the surface is cooled in the molding process. That is, the outer peripheral surface of the cylindrical cover portion (grip) of the existing gas sensor, which has a simply cylindrical and smooth shape, is likely to have defects, such as recesses and bulges, after being molded. Thus, the existing gas sensor, whose surface is smooth, has a problem in that decrease in the quality of appearance is likely to occur, and a molding defect, such as an appearance defect and low dimensional accuracy, may occur.

SUMMARY OF THE INVENTION

An object of the present invention, which has been devised to solve the problems described above, is to provide a gas sensor that includes a protective cover having a resin cylindrical cover portion at a rear end thereof and that can be press-fitted into and airtightly attached to an attachment hole by an operator by holding the cylindrical cover portion with his/her fingers while twisting the sensor. With the gas sensor, decrease in the quality of the appearance of the cylindrical cover portion and occurrence of a molding defect is reduced, and the press-fitting attachment operation can be performed smoothly.

According to an aspect of the present invention, a gas sensor, which is to be airtightly attached to an attachment hole in an object, includes an annular or tubular metal shell; a ring-shaped elastic sealing member, for airtight sealing, that is mounted on an outer peripheral surface of the metal shell; a detection element that is disposed in the metal shell; a metal terminal that is electrically connected to the detection element; and a protective cover that is fixed to a rear end of the metal shell or a portion of the metal shell adjacent to the rear end so as to be unrotatable around an axis of the metal shell, the protective cover covering a rear end of the detection element and the metal terminal. The protective cover includes a resin cylindrical cover portion that has an axis that is substantially the same as or parallel to the axis of the metal shell, the cylindrical cover portion serving as a grip when attaching the gas sensor to the attachment hole. The cylindrical cover portion includes a plurality of vertical ribs on an outer peripheral surface thereof, the vertical ribs extending substantially parallel to the axis of the cylindrical cover portion so that protrusions and recesses are formed in a circumferential direction.

The gas sensor may further include a metal tube that is integrated with the resin cylindrical cover portion by being insert molded with the resin cylindrical cover portion so that an axis of the metal tube is the same as or substantially parallel to the axis of the cylindrical cover portion and so that an outer peripheral surface of at least a rear portion of the metal tube is surrounded by and embedded in the cylindrical cover portion. The protective cover is fixed to the portion of the metal shell adjacent to the rear end of the metal shell at a front end of the tube or a portion of the tube adjacent to the front end. The cylindrical cover portion may include a horizontal rib that extends in the circumferential direction and that bulges on a portion of the outer peripheral surface of the cylindrical cover portion surrounding the outer peripheral surface of the tube.

In the gas sensor, the horizontal rib may be formed at a front end of the cylindrical cover portion.

In the gas sensor according to the present invention, the cylindrical cover portion of the protective cover includes the plurality of vertical ribs on an outer peripheral surface thereof, the vertical ribs extending substantially parallel to the axis of the cylindrical cover portion so that protrusions and recesses are formed in the circumferential direction. In an existing cylindrical cover portion, due to a simply cylindrical shape and a smooth outer peripheral surface thereof, defects, such as recesses and bulges, are likely to be formed on the outer peripheral surface in a resin molding process. In contrast, with the present invention, because the cylindrical cover portion includes the vertical ribs, occurrence of such defects can be reduced. As a result, with the present invention, decrease in the quality of the appearance of the cylindrical cover portion can be reduced, and occurrence of a molding defect, such as an appearance defect of the cylindrical cover portion and low dimensional accuracy, can be reduced, and therefore the production yield of the protective cover can be increased.

When press-fitting the gas sensor according to the present invention into an attachment hole in an object, an operator grips the cylindrical cover portion with his/her fingers and first inserts the front end of the gas sensor into the attachment hole. In the process of press-fitting the gas sensor, because the cylindrical cover portion of the gas sensor has the vertical ribs on the outer peripheral surface, the operator can easily grip and twist the cylindrical cover portion, as compared with a case where the cylindrical cover portion does not have the vertical ribs. That is, the operator can easily twist the cylindrical cover portion, because the operator's fingers are not likely to slip when twisting the cylindrical cover portion. Therefore, the operation of attaching the sensor can be smoothly performed, and the attachment process can be performed more easily and rapidly. In the present invention, the meaning of the term "cylindrical" in "cylindrical cover portion" is not limited to the shape of a cylinder that has a uniform diameter in the front-rear direction but also includes the shape of a tapered cylinder or the like. In the present application and the present invention, regarding a gas sensor, the term "front end" refers to an end of the gas sensor that is inserted into a deeper position in the attachment hole, and the term "rear end" refers to an end opposite to the front end. Regarding elements of a gas sensor, the term "front end" refers to an end closer to the "front end" of the gas sensor, and the term "rear end" refers to an end opposite to the front end.

The meaning of the term "cylindrical" in the "resin cylindrical cover portion" includes the meaning that the shape of the cover portion can be regarded as "cylindrical" when other elements that are integrally formed with the outer peripheral surface of the cylindrical cover portion are removed. Examples of such elements include a cover (connector terminal cover), which covers connection terminals to be connected to external wires, and a bracket for fixing the sensor. The meaning of the term "cylindrical" also includes the shape of a cylinder whose length in the front-rear direction differs in accordance with a position in the circumferential direction thereof. For example, the length of the cylindrical shape may be shorter in regions in which such elements are disposed. That is, in the present invention, for example, a resin connector terminal cover may be integrally formed with the outer peripheral surface of the cylindrical cover portion so as to protrude outward (in the radial direction). In this case, the length in the front-rear direction of the outer peripheral surface of the cylindrical cover portion in a region on which the terminal cover portion is formed is reduced or becomes zero due to the presence of the terminal cover portion. Therefore, an operator can hold only a small part of the outer peripheral surface in the front-rear direction or cannot hold the outer peripheral surface when press-fitting the gas sensor. The cylindrical cover portion of the gas sensor may include a screw bracket that protrudes from the other peripheral surface at a position different from the position of the connector terminal cover. The screw bracket, which allows the gas sensor to be fixed to an object with a screw, is used to prevent accidental removal of the sensor from an attachment hole, which may occur when the gas sensor is only press-fitted into the attachment hole. The screw bracket is attached to a position on the outer peripheral surface of the cylindrical cover portion that is different from the position where the connector terminal cover is attached. The above description about the connector terminal cover also applies to this case. Thus, in the present invention, the meaning of the term "cylindrical" of the "cylindrical cover portion" includes meanings in the cases where the connector terminal cover and the like are disposed on the outer peripheral surface of the cylindrical cover portion.

The vertical ribs may extend over the entire length of the outer peripheral surface of the cylindrical cover portion in the axial direction, may extend over a part of the length of the outer peripheral surface, or may be divided in the axial direction. The vertical ribs may be modified as long as they have the effect of suppressing slipping of fingers when an operator holds or grips the cylindrical cover portion and twists the cylindrical cover portion. The height to which the vertical ribs bulge (protrude) from the outer peripheral surface of the cylindrical cover portion, the width of the vertical ribs in the circumferential direction, and the number of the vertical ribs may be appropriately determined so that the effect of suppressing slipping can be obtained. Preferably, the height and the width of the vertical ribs are determined in consideration of the thickness and the like of parts of the cylindrical cover portion so that an excessively large difference in contraction may not occur when a molding resin is cooled to form the vertical ribs. Preferably, corners between the outer peripheral surface of the cylindrical cover portion and side surfaces of the vertical ribs, which bulge on the outer peripheral surface, are rounded as appropriate, and corners of the vertical ribs are chamfered as appropriate. By doing so, a die can be more reliably filled with a resin and the appearance of the cylindrical cover portion can be improved.

In the case where the gas sensor according to the present invention includes a metal tube as described above, the metal tube is embedded in the cylindrical cover portion of the protective cover by insert molding the protective cover by using the metal tube as an insert. In this case, the protective cover can be securely fixed to the metal shell by welding the metal tube to the metal shell. Moreover, because heat of the gas to be detected, which is transferred from the metal shell, can be dissipated from the exposed portion of the tube, thermal degradation of a resin of the protective cover can be suppressed. That is, the tube also functions as a heat sink. Furthermore, in this case, not only the protective cover is insert molded by using the metal tube as an insert, but also the protective cover has the horizontal rib. Therefore, the cylindrical cover portion can be made to closely contact the tube and the airtightness can be increased. Accordingly, the risk of gas leakage due to insert molding can be reduced. This is because, when the horizontal rib is present, the outer peripheral surface of the tube can be more tightly pressed when the resin is cooled and contracts in insert molding than a case when the horizontal rib it not present. In order to increase closeness of contact and airtightness, preferably, the height to which the horizontal rib bulges and the width of the horizontal rib in the front-rear direction are large, and the horizontal rib is formed along the entire circumference of the cylindrical cover portion.

For ease of gripping the cylindrical cover portion and improvement of closeness of contact, as described above, the horizontal rib is preferably formed at the front end or a portion of the cylindrical cover portion adjacent to the front end. In the present invention, the resin material of the cylindrical cover portion may be selected from resins having appropriate strength, heat resistance, and moldability.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

Figure 1:
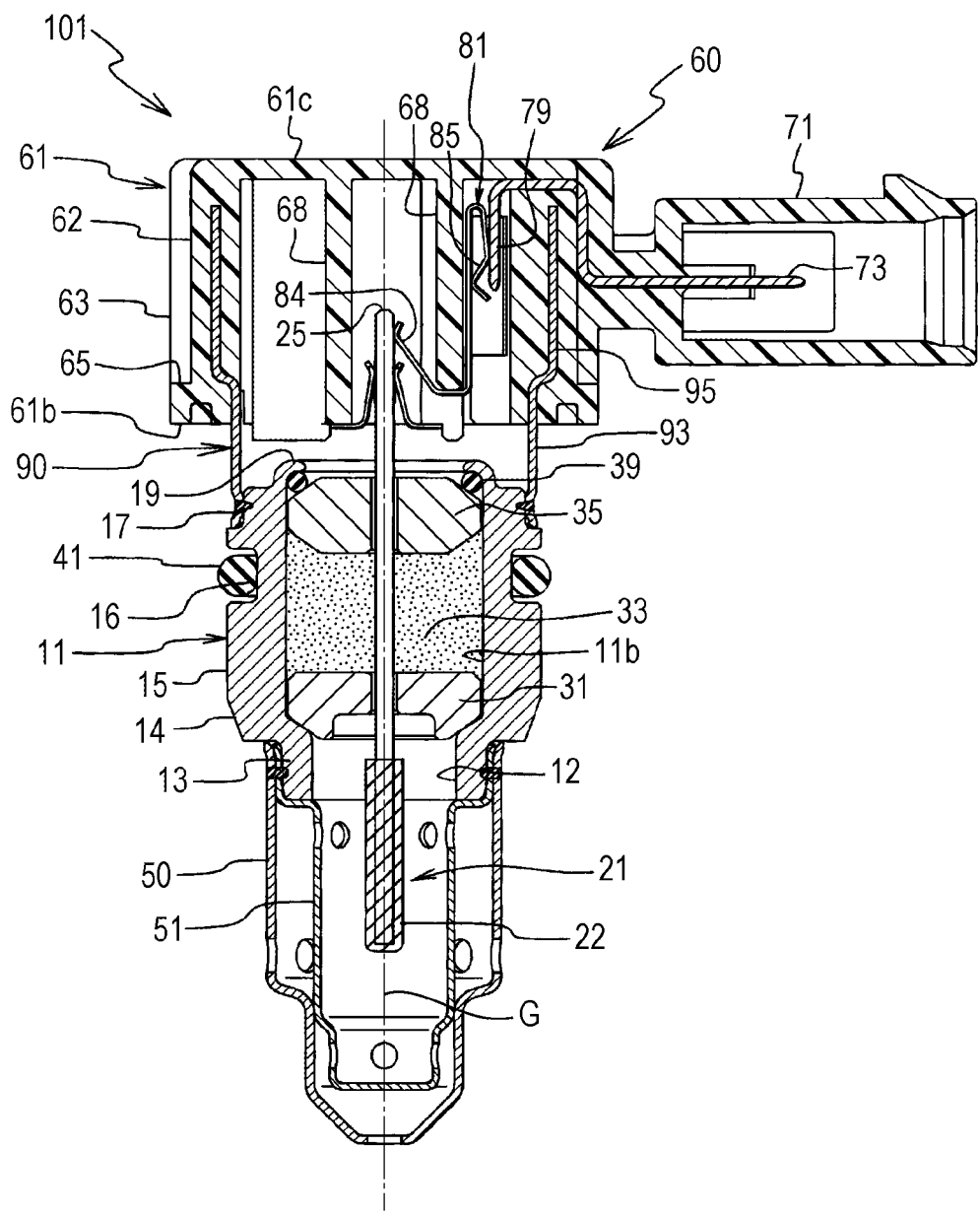
FIG. 1 is a front longitudinal sectional view of a gas sensor according to an embodiment of the present invention.
Figure 2:
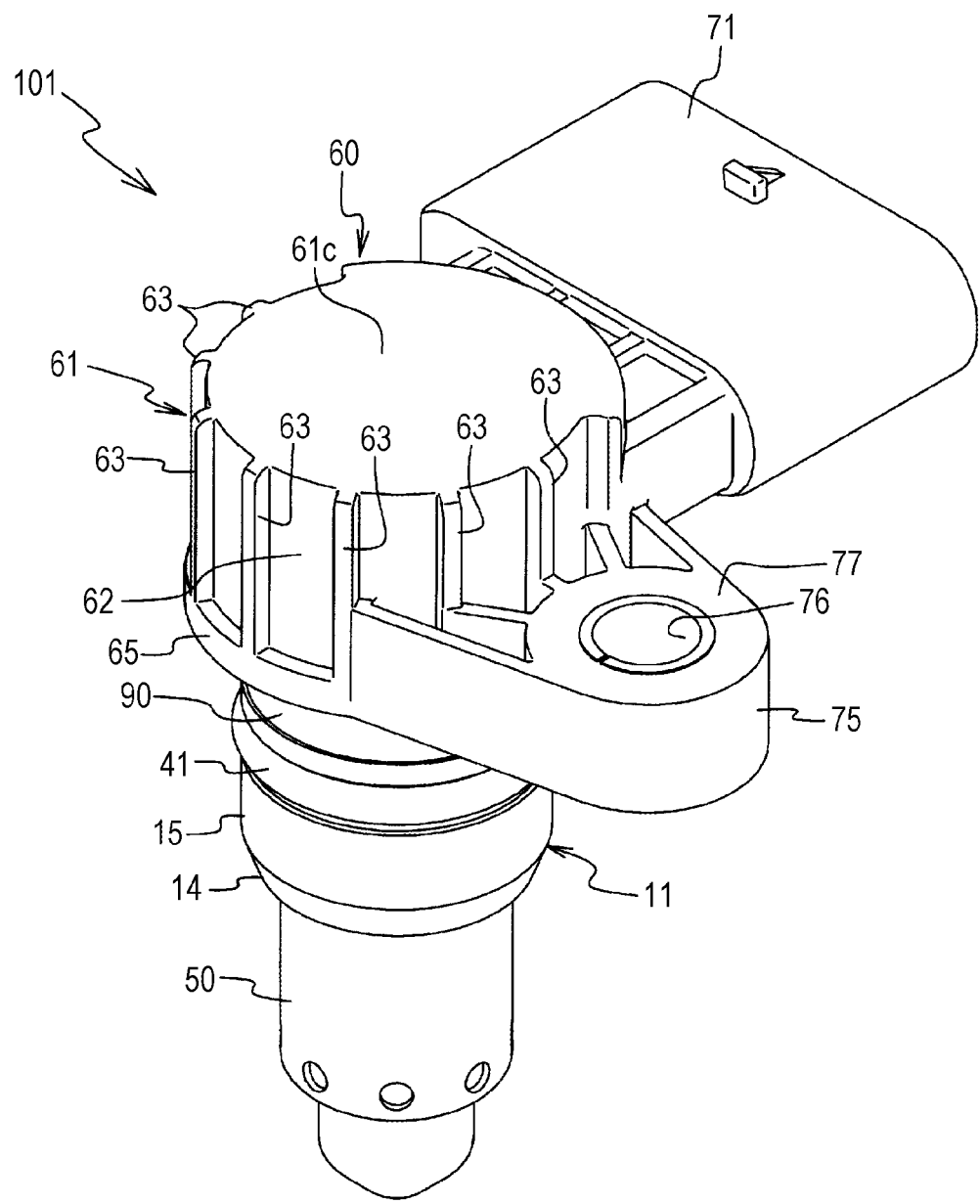
FIG. 2 is an external perspective view of the gas sensor of FIG. 1.

Referring to FIGS. 1 to 7, a gas sensor acceding to an embodiment of the present invention will be described in detail. The gas sensor according to the present embodiment is a wideband air-fuel ratio sensor for detecting the concentration of oxygen in a gas. As illustrated in FIG. 1, a gas sensor 101 includes a metal shell 11, a detection element 21, and a protective cover 60. The metal shell 11 (also referred to as a "shell 11") has a tubular shape (stepped cylindrical shape). The detection element 21 is disposed in the metal shell 11, extends in the front-rear direction, and has a rear end 25 (see FIGS. 1 and 6) protruding rearward from the rear end (in FIG. 1, the upper end) of the shell 11. The protective cover 60 is fixed to the rear end of the shell 11 so as to cover the rear end 25 of the shell 11, and electrical connection means connected to the element 21, and the like. Hereinafter, these components will be described in detail.

An inner peripheral surface 11b of the metal shell 11 of the sensor 101, excluding a small diameter portion 12 adjacent to the front end of the metal shell 11, forms a cylindrical hole (circular hole) having a uniform diameter in the front-rear direction. A holder 31 is disposed at the rear end (an annular rearward-facing surface) of the small diameter portion 12 of the inner peripheral surface 11b. The holder 31 is made of an insulating material (such as alumina), has a through-hole extending in the front-rear direction, and has such an outside diameter that the holder 31 can be loosely fitted into the shell 11. The detection element 21, which has a strip-like (or bar-like) shape, extends through the through-hole in the holder 31. A front end of a detection portion 22, which is located adjacent to the front end of the detection element 21, protrudes forward from the front ends of the holder 31 and the shell 11 (the lower ends in FIG. 1).

The through-hole in the holder 31 has a cross-sectional shape corresponding to the (quadrangular) cross-sectional shape of the detection element 21. The detection element 21, which extends through the through-hole, is fixed to the inside of the metal shell 11 so as to be airtight in the front-rear direction. The detection element 21 is fixed by pressing a sealing material 33 (such as talc powder) disposed on the rear side (the upper side in FIG. 1) of the holder 31 in the direction of the axis G of the shell 11 (toward the front side) by using a pressing member 35, which is made of an insulating material and has a through-hole. The outside diameter and the shape of the through-hole of the pressing member 35 are the same as those of the holder 31. The pressing member 35 can continue pressing the sealing material 33 because a rear end portion (also referred to as a "crimping cylindrical portion 19") of the shell 11 is crimped. The crimping cylindrical portion 19 is crimped by being bent inward so as to compressively deform (press) the pressing member 35 forward with a ring washer 39 therebetween.

The outer peripheral surface of the metal shell 11 is as follows. The metal shell 11 includes a small-diameter portion 13, a tapered tube portion 14, a straight tube portion 15, a protective-cover-fixing annular portion 17 (a portion of the shell adjacent to the rear end of the shell), and a crimping cylindrical portion 19. The small-diameter portion 13, to which protectors (described below) are to be attached, is located at a front end portion of the metal shell 11 corresponding to the aforementioned small diameter portion 12. The tapered tube portion 14, whose diameter increases rearward, is disposed on the rear side of the small-diameter portion 13. The straight tube portion 15, which has a uniform diameter in the front-rear direction, is disposed in a middle portion of the outer peripheral surface adjacent to the back end of the tapered tube portion 14. The protective-cover-fixing annular portion 17 has a smaller diameter than the straight tube portion 15. The crimping cylindrical portion 19 is disposed at the rear end of the protective-cover-fixing annular portion 17 and has a smaller diameter and thickness than the protective-cover-fixing annular portion 17. In the gas sensor 101 shown in FIG. 1 and other figures, the crimping cylindrical portion 19 is bent inward and compressively deformed forward, because a crimping process, for compressively holding the sealing material 33, has been performed on the crimping cylindrical portion 19. The cross-sectional shapes of the shell 11, which has different diameters in the front-rear direction, are concentric circles centered at the axis G.

Figure 3:
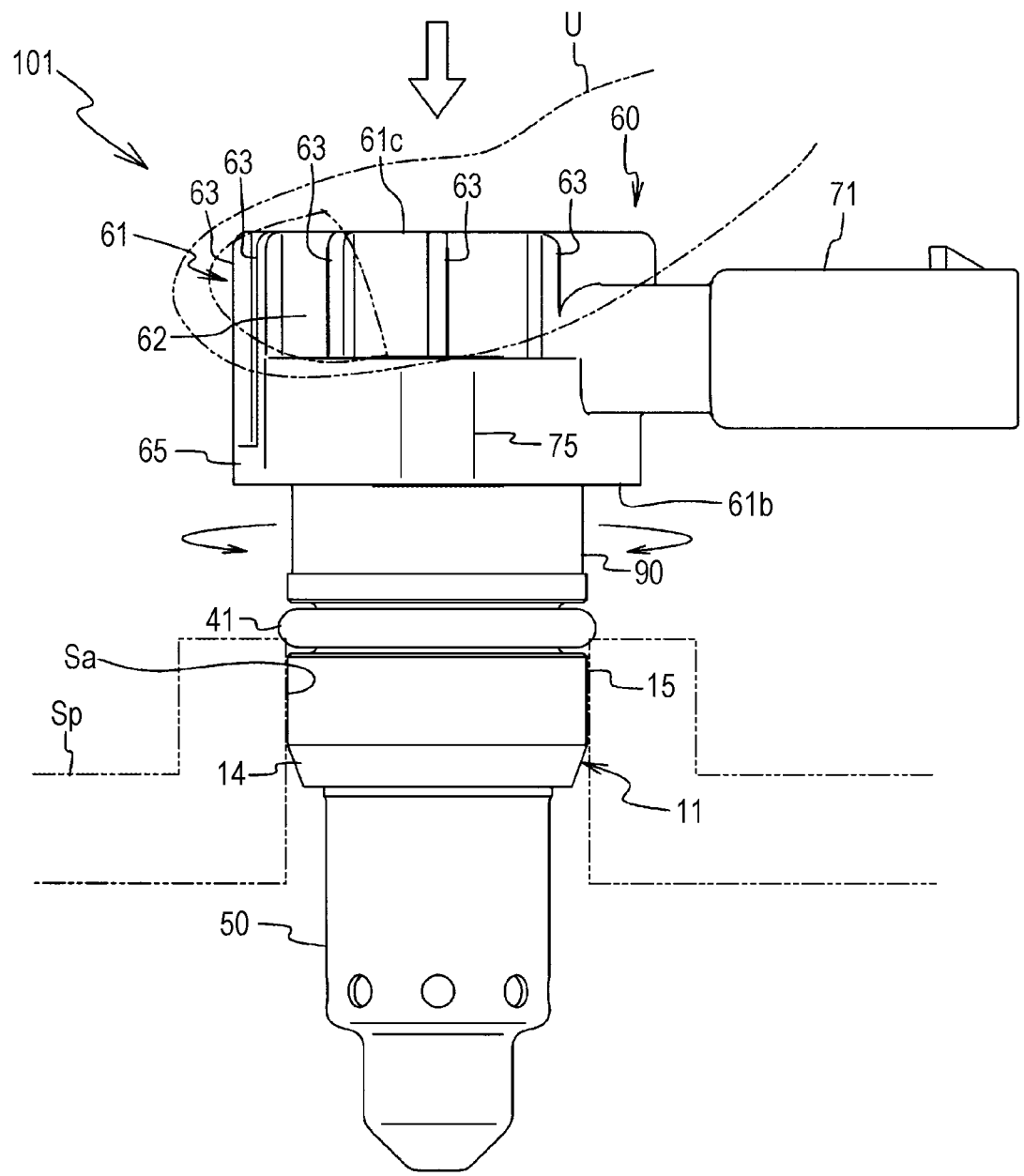
FIG. 3 illustrates the gas sensor of FIG. 1 when being press-fitted into an attachment hole in an object.
Figure 4:
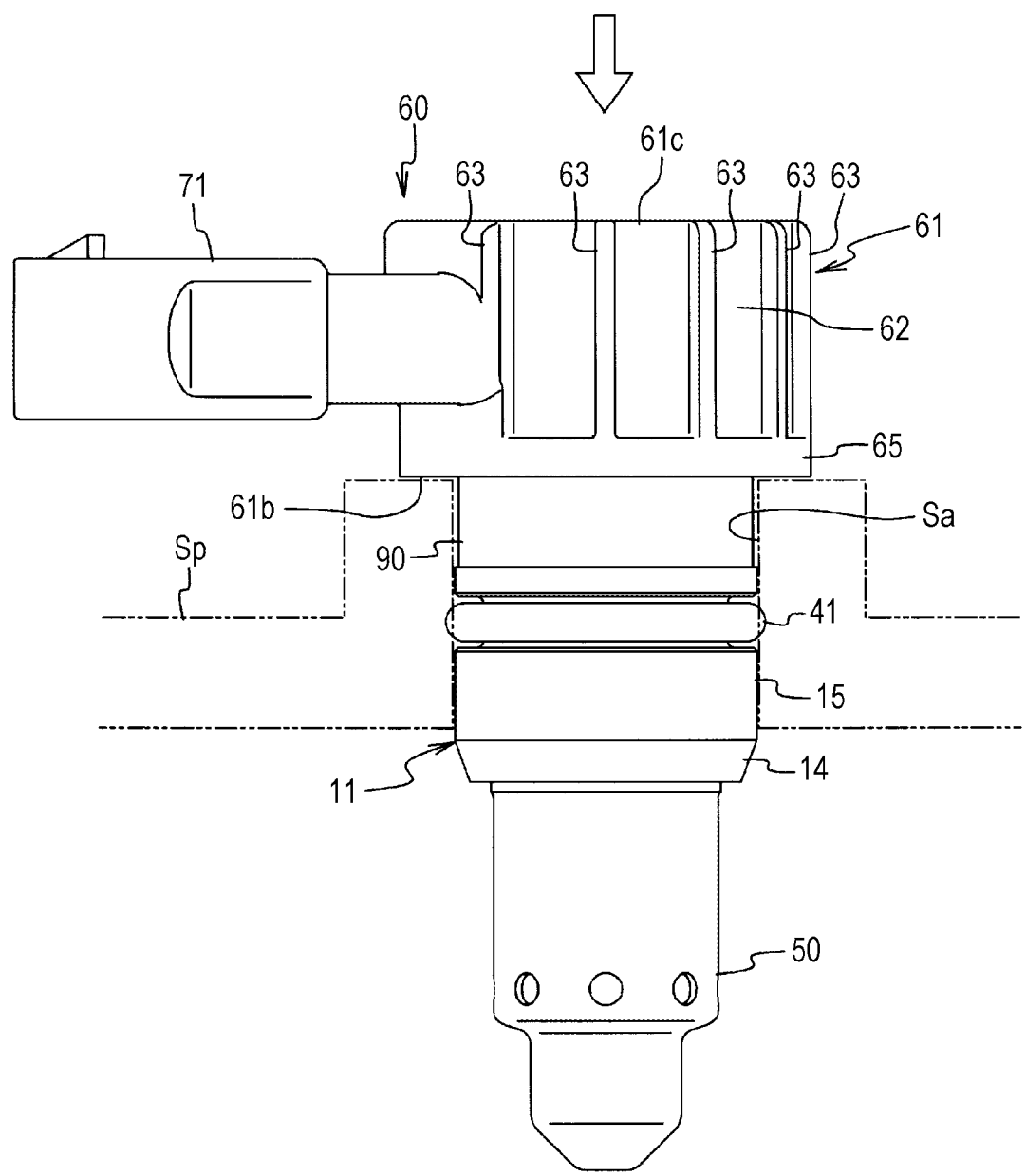
FIG. 4 is a rear view of the gas sensor of FIG. 1 after having been press-fitted into the attachment hole in the object.

A ring-shaped groove 16, extending in the circumferential direction, is formed in a part of the outer peripheral surface of the metal shell 11 adjacent to the rear end of the straight tube portion 15, which has a larger diameter. A ring-shaped elastic sealing member 41 is fitted and mounted into the ring-shaped groove 16. In the present embodiment, the elastic sealing member 41, which needs to have a sealing ability due to elasticity, is a rubber packing having appropriate elasticity, strength, and heat resistance. In the present embodiment, when the gas sensor 101 is press-fitted into and attached to an attachment hole Sa (circular hole) in an object (such as an intake pipe of an engine) via the metal shell 11 as illustrated in FIGS. 3 and 4, the ring-shaped elastic sealing member 41 maintains airtightness. The outside diameter of the straight tube portion 15 is slightly smaller than the inside diameter of the attachment hole Sa. In order to obtain airtightness, the elastic sealing member 41 needs to be compressively deformed appropriately in the radial direction of the hole after the gas sensor 101 has been attached to an object. Therefore, the elastic sealing member 41 is configured so that, when the elastic sealing member 41 is mounted in the ring-shaped groove 16 (and before the gas sensor 101 is press-fitted into the attachment hole), the outside diameter of the elastic sealing member 41 is larger than the inside diameter of the attachment hole Sa by an appropriate amount and has appropriate deformability. The tapered tube portion 14 of the shell 11 serves as a guide when attaching the gas sensor 101 to the attachment hole Sa in the object.

As described above, a portion of the element 21 adjacent to the rear end 25, including the rear end 25, protrudes rearward from the rear ends of the pressing member 35 and the metal shell 11. Metal terminals 81, each having spring properties, are pressed against and electrically connected to electrode terminals (not shown), which are formed on the portion of the element 21 adjacent to the rear end 25. The metal terminals 81 are electrically connected to pin terminals 73, which protrude in a connector terminal cover 71 of the protective cover 60 as described below, so that the element 21 can be connected lead wires (not shown) outside the gas sensor 101. The protective cover 60 is fixed to the protective-cover-fixing annular portion 17, which is a portion of the metal shell 11 adjacent to the rear end of the metal shell 11, so as to cover the rear end 25 of the detection element 21 and the metal terminals 81 for electrical connection to the detection element 21. The protective cover 60 and the connector terminal cover 71 and the like, which are integrated with the protective cover 60, will be described below in detail.

The detection element 21, which is a strip-shaped element (having a rectangular cross section) elongated in the front-rear direction, includes a detection portion 22 having detection electrodes and the like (not shown) in a front end portion thereof, which is to be pointed toward a measurement object. The detection element 21 is mainly composed of a solid electrolyte and a ceramic material. A portion of the element 21 adjacent to the front end thereof, extending rearward by a predetermined length from the front end, is coated with a porous protective layer, which is made of alumina, spinel, or the like. The detection element 21, which is the same as exiting detection elements, includes the detection portion 22 and electrode terminals (not shown) for outputting a detection signal. The detection portion 22, which includes a pair of detection electrodes, is disposed at a portion of a solid electrolyte adjacent to the front end of the solid electrolyte. The electrode terminals are disposed adjacent to the rear end 25 and connected to the detection electrodes of the detection portion 22. In the present embodiment, a heater (not shown) is disposed in a portion of the element 21 adjacent to the front end of a multilayered ceramic member formed in the solid electrolyte. Electrode terminals, to which lead wires for applying a voltage to the heater are to be connected, are formed so as to be exposed on a portion of the element 21 adjacent to the rear end. Although not illustrated, three or two of these electrode terminals, each having a vertically elongated rectangular shape, are arranged side by side on both wide surfaces of a portion of the strip-shaped element 21 adjacent to the rear end 25.

Protectors 50 and 51 are fitted onto and fixed by welding or the like to the small-diameter portion 13 at the front end of the metal shell 11 of the sensor 101. The protectors 50 and 51, each having a tubular shape with a bottom, surround a portion of the element 21 adjacent to the front end of the element 21, including the detection portion 22, and protects the detection portion 22 from, for example, being covered with water. Two protectors 50 and 51 are used to reinforce protection ability. Holes (vent holes) are formed at appropriate positions in the protectors 50 and 51 so that a gas can contact the detection portion 22 and circulate and pass through the space in the protectors 50 and 51.

The protective cover 60 covers the rear end 25 of the detection element 21, which is exposed on the rear side of the metal shell 11, and the metal terminals 81, which are electrically connected to the element 21. The protective cover 60 is fixed (welded) to the protective-cover-fixing annular portion 17 adjacent to the rear end of the metal shell 11. The protective cover 60 includes a cylindrical cover portion 61 made of a resin. The cylindrical cover portion 61 serves as a grip when attaching the gas sensor 101 to the attachment hole Sa by a press-fitting method. A tube 90 is embedded in the cylindrical wall of the cylindrical cover portion 61 in such a way that a front portion thereof protrudes from a front end 61*b* of the cylindrical cover portion 61. The tube 90 is coaxial with the cylindrical cover portion 61 and made of a metal (such as a stainless steel). The tube 90 is embedded in the cylindrical wall by insert molding the protective cover 60, including the cylindrical cover portion 61 made of a resin. The tube 90 is coaxially fixed to the shell 11 by welding the front end of the tube 90 to the protective-cover-fixing annular portion 17, which is adjacent to the rear end of the shell 11, in the circumferential direction. Thus, the shell 11 and the cylindrical cover portion 61 are coaxial with each other. In the present embodiment, the tube 90, which has a stepped cylindrical shape, includes a small-diameter portion 93 in a front portion thereof and a large-diameter portion 95 in a rear portion thereof. The large-diameter portion 95 and a part of the small-diameter portion 93 are embedded in the cylindrical cover portion 61. Most of the small-diameter portion 93 protrudes forward from the front end of the cylindrical cover portion 61. The front end of the small-diameter portion 93 is fitted onto and welded to the protective-cover-fixing annular portion 17, which is adjacent to the rear end of the shell 11, in the circumferential direction.

In the state in which the protective cover 60 is fixed to the shell 11, the metal terminals 81 are disposed in an opening in the cylindrical cover portion 61 adjacent to the front end 61*b* (the lower end in the figures). The metal terminals 81 are electrically connected to electrode terminals that are disposed on a portion of the element 21 adjacent to the rear end 25, which is inserted into a substantially central portion of the opening. In the present embodiment, the connector terminal cover 71, which is made of a resin, is disposed on a middle portion of one side (the right side in FIG. 1) of an outer peripheral surface 62 of the cylindrical cover portion 61 in the front-rear direction. The connector terminal cover 71 is integrally formed with the cylindrical cover portion 61. The metal terminals 81 are electrically connected the pin terminals 73 (male pins) that are disposed in the connector terminal cover 71 (socket portion) so as to protrude outward. In the present embodiment, a bracket 75 for fixing the sensor 101 is disposed on a portion of the outer peripheral surface 62 of the cylindrical cover portion 61 adjacent to the front end of the outer peripheral surface 62 (see FIG. 2). The bracket 75 protrudes in a direction perpendicular to the connector terminal cover 71 when seen from the rear side. A circular hole 76 is formed in a portion of the bracket 75 adjacent to the front end of the bracket 75 so as to extend through the portion in the front-rear direction. The circular hole 76 is used to fix the sensor 101 to an object with a screw. When seen from the rear side, the bracket 75 has a rib structure in which a top plate 77 (rear plate portion) of the bracket 75, which has the circular hole and has a tapered shape, is connected to the outer peripheral surface 62 of the cylindrical cover portion 61 through five ribs. The structure of the inside of the cylindrical cover portion 61 and electrical connection between the terminals will be described below in detail.

A plurality of vertical ribs 63 are formed on the outer peripheral surface 62 of the cylindrical cover portion 61 of the protective cover 60 of the sensor 101. The vertical ribs 63, which are made from the same resin by injection molding, are arranged at regular intervals in the circumferential direction and extend in the direction of the axis G of the cylindrical cover portion 61 so that protrusions and recesses are arranged in the circumferential direction. The vertical ribs 63 may be formed on the entirety of the outer peripheral surface 62 of the cylindrical cover portion 61 in the circumferential direction (on the entire circumference). However, in the present embodiment, because the connector terminal cover 71 (socket portion) protrudes from the middle portion of the outer peripheral surface 62 in the front-rear direction, the vertical ribs 63 are not formed on the portion on which the cover 71 is disposed. Some of the vertical ribs 63, which have a smaller length in the front-rear direction, are disposed on a rear portion of a part of the outer peripheral surface 62 of the cylindrical cover portion 61 on which the bracket 75 is disposed (see FIG. 2). Thus, when an operator holds the cylindrical cover portion 61 with fingers of one of his/her hand, the surfaces of the fingers are depressed along the vertical ribs 63, and the operator can twist the cylindrical cover portion 61 by securely holding the vertical ribs 63. That is, the cylindrical cover portion 61, having the vertical ribs 63 on the outer peripheral surface 62, is less likely to slip as compared with a case where the cylindrical cover portion does not have vertical ribs, and the operator can be securely grip the cylindrical cover portion 61. In the present embodiment, a horizontal rib 65 (thick portion) is formed in the circumferential direction on a part of the outer peripheral surface 62 continuous with an opening edge (the lower end in FIG. 2). The horizontal rib 65 budges to the same height (protruding length) as the vertical ribs 63 and has a predetermined width in the front-rear direction. The front end 61*b* of the cylindrical cover portion 61 of the sensor 101 serves as a stopper when attaching the sensor 101 to the attachment hole Sa in the object Sp.

As described above, in the present embodiment, the cylindrical cover portion 61 of the protective cover 60 of the sensor 101 includes the vertical ribs 63, which extend in a direction substantially parallel to the axis of the cylindrical cover portion 61, on the outer peripheral surface 62 so that protrusions and recesses are formed in the circumferential direction. Thus, the cylindrical cover portion 61 is less likely to slip, and an operator can securely grip the cylindrical cover portion 61 as compared with a case where the cylindrical cover portion 61 does not have the vertical ribs 63. In addition, the vertical ribs 63 bring the following advantages. That is, in contrast to cylindrical cover portions of existing protective covers, which have a simply cylindrical smooth outer peripheral surface, because the cylindrical cover portion 61 of the protective cover 60 of the sensor 101 according to the present embodiment has the vertical ribs 63, occurrence of defects of the outer peripheral surface 62, such as depressions and bulges, can be reduced. As a result, the quality of the appearance of the cylindrical cover portion 61 can be improved. Furthermore, because the occurrence of defects, such as appearance defect and low dimensional accuracy, can be reduced, the production yield of the protective cover 60 can be increased.

As illustrated in FIGS. 3 and 4, the sensor 101, structured as described above, is press-fitted into an attachment hole Sa in an object Sp, such as a part of an intake system of an engine. That is, as shown by a two-dot chain line in FIG. 3, an operator usually grips or holds the cylindrical cover portion 61 of the sensor 101 with fingers U of one of his/her hand, and first inserts a front end portion of the sensor 101, including the protectors 50 and 51, into the attachment hole Sa. Because the elastic sealing member 41 is attached to the outer peripheral surface of the metal shell 11, it is necessary to press-fit the sensor 101 into the attachment hole Sa. Therefore, it is necessary to press the sensor 101 into the attachment hole Sa against a force generated by deformation of the elastic sealing member 41 until the sensor 101 reaches a predetermined position as shown in FIG. 4. At this time, the operator twists the cylindrical cover portion 61 of the protective cover 60 in the circumferential direction as necessary. Because the vertical ribs 63 are formed on the outer peripheral surface 62, the surfaces of the fingers of the operator holding the cylindrical cover portion 61 are depressed by the vertical ribs 63. As a result, the cylindrical cover portion 61 is not likely to slip when twisted, as compared with a case where the vertical ribs 63 are not formed on the outer peripheral surface 62. Accordingly, the operator can smoothly perform the press-fitting operation. As a result, the sensor 101 can be easily and rapidly press-fitted into and attached to the object.

In the present embodiment, the sensor 101 includes the bracket 75 having the circular hole 76. After the sensor 101 has been press-fitted, a screw is screwed into the object Sp through the circular hole 76. By doing so, the metal shell 11 of the sensor 101 is prevented from being rotated in the attachment hole Sa, and accidental removal of the sensor 101 can be prevented. Preferably, a metal pipe is disposed in the circular hole 76 by insert molding using the pipe as an insert so that the circular hole 76 has a metallic inner peripheral surface.

In the present embodiment, the metal tube 90 is embedded, as an insert, in the cylindrical cover portion 61 of the protective cover 60. The protective cover can be securely fixed to the metal shell 11, because the metal tube 90 is welded to the metal shell 11. Moreover, because heat of a gas to be measured, which is transferred from the metal shell 11, can be dissipated from the exposed portion of the tube 90, thermal degradation of a resin material of the protective cover 60 can be suppressed. In a case where thermal degradation of a resin is not a problem, it is not necessary to use the tube 90, and, for example, a front end of the cylindrical cover portion 61 may be directly joined and fixed to the rear end of the metal shell 11 or a portion of the metal shell 11 adjacent to the rear end. This may be performed by inert molding the cylindrical cover portion 61 by using the metal shell 11 as an insert.

In the present embodiment, when insert molding the cylindrical cover portion 61 by using the metal tube 90 as the insert, the horizontal rib 65 is formed at the front end 61b of the outer peripheral surface 62 in the circumferential direction. Therefore, the cylindrical cover portion 61 and the outer peripheral surface of the tube 90 can tightly contact each other, so that decrease of airtightness, which might occur in an insert molding process, can be prevented. A base portion of the bracket 75, which protrudes, have the same effect. In the present embodiment, the tube 90 has a stepped cylindrical shape and has the small-diameter portion 93 in a front portion thereof, and a part of the tube 90, including the boundary between the small-diameter portion 93 and the large-diameter portion 95, is embedded in a resin. Therefore, the tube 90 can be securely fixed to the cylindrical cover portion 61. In the present embodiment, the connector terminal cover 71 is integrally formed with the cylindrical cover portion 61. Alternatively, the connector terminal cover 71 may be omitted, and lead wires may be drawn to the outside from the cylindrical cover portion 61. In the present embodiment, the bracket 75 is integrally formed with the cylindrical cover portion 61. However, in a case where another fixing means is used, the bracket 75 is not necessary.

Figure 5:
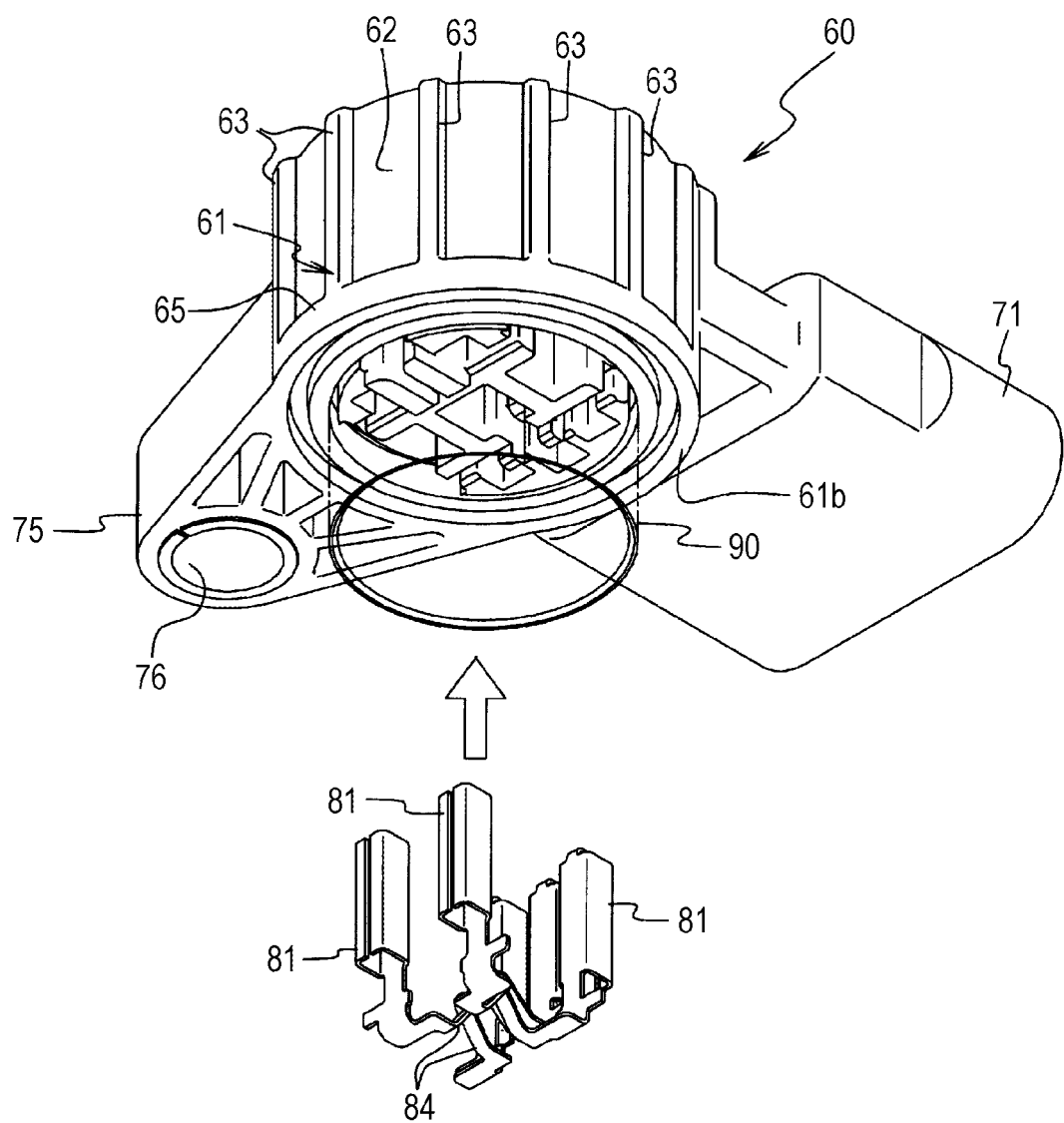
FIG. 5 is an exploded perspective view illustrating a protective cover of the gas sensor of FIG. 1 and metal terminals, which are accommodated in predetermined spaces in the protective cover, seen from the front side.

Here, the structure of the inside of the cylindrical cover portion 61 of the protective cover 60 according to the embodiment and how the terminals are electrically connected to each other will be described in detail. The cylindrical cover portion 61 of the protective cover 60, which has a cylindrical cap-like shape, includes a flat plate 61c at the rear end thereof (the upper end in the figures) and the inside of the front end 61b (the lower end in the figures) is open. As illustrated in FIGS. 1 and 5 and an upper part of FIG. 6, the opening in the cylindrical cover portion 61 includes a central space, into which the rear end 25 of the element 21 is inserted, and spaces on both sides of the element 21. The metal terminals 81, which are connected to electrode terminals of the element 21, are accommodated in the spaces so as to be insulated from each other. Separation walls 68 (insulating separation walls) are formed in a grid-like shape so that the spaces are separated from each other when the cylindrical cover portion 61 is seen from the open side (see FIG. 5). Each of the metal terminals 81, which is disposed beforehand in a corresponding one of the spaces separated by the insulating separation walls 68 (separators), includes a first spring piece 84 (contact piece), which has spring properties, at one end thereof. The first spring pieces 84 are pressed against corresponding electrode terminals, which are formed on both surfaces of a portion of the element 21 adjacent to the rear end 25 inserted into the central space, so that the metal terminals 81 are electrically connected to the electrode terminals (see FIGS. 1, 5, and 6).

In the present embodiment, as described above, the connector terminal cover 71 is integrally formed with the cylindrical cover portion 61 on one side of the outer peripheral surface 62. The pin terminals 73 (male pins), which are disposed in the cover 71 so as to protrude outward, are embedded in the cover 71 by performing inert molding by using the pin terminals 73 as inserts, as with the metal tube 90. Each of the metal terminals 81, through which the pin terminals 73 are connected to the electrode terminals of the element 21, includes a second spring piece 85 (contact piece), which have spring properties, at the other end (rear end) thereof. As illustrated in FIG. 1, when the metal terminals 81 are disposed in corresponding openings in the cylindrical cover portion 61, the second contact pieces 85 are pressed against and electrically connected to inner end portions 79 of the corresponding pin terminals 73. That is, the metal terminals 81, which include the first contact pieces 84 to be pressed against the electrode terminals of the element 21 and the second contact pieces 85 to be pressed against the pin terminals 73 in the connector terminal cover 71, are disposed in corresponding accommodation spaces in the cylindrical cover portion 61 and are electrically connected to the pin terminals 73. Each of the metal terminals 81 is made by bending a thin metal plate having spring properties (see FIG. 5).

An end portion, opposite to the protruding end portion, of each of the pin terminals 73 in the connector terminal cover 71 is, for example, bent rearward and then bent forward into a U-shape. The inner end portion 79, which is a leg portion (terminal) at a free end of the U-shaped portion, is exposed in a corresponding one of the accommodation spaces (see FIG. 1). Thus, when the metal terminals 81 are disposed in the corresponding accommodation spaces, the second contact pieces 85 are pressed against the inner end portions 79, which are leg portions (terminals) of the pin terminals 73 adjacent to the free ends of the U-shaped pin terminals 73. The first contact pieces 84 of the metal terminals 81, which are disposed in the accommodation spaces, are basically bent rearward in the central space in which the rear end 25 of the element 21 is accommodated. The first contact pieces 84 are pressed against electrode terminals, which are disposed on a portion of the element 21 adjacent to the rear end 25.

Figure 6:
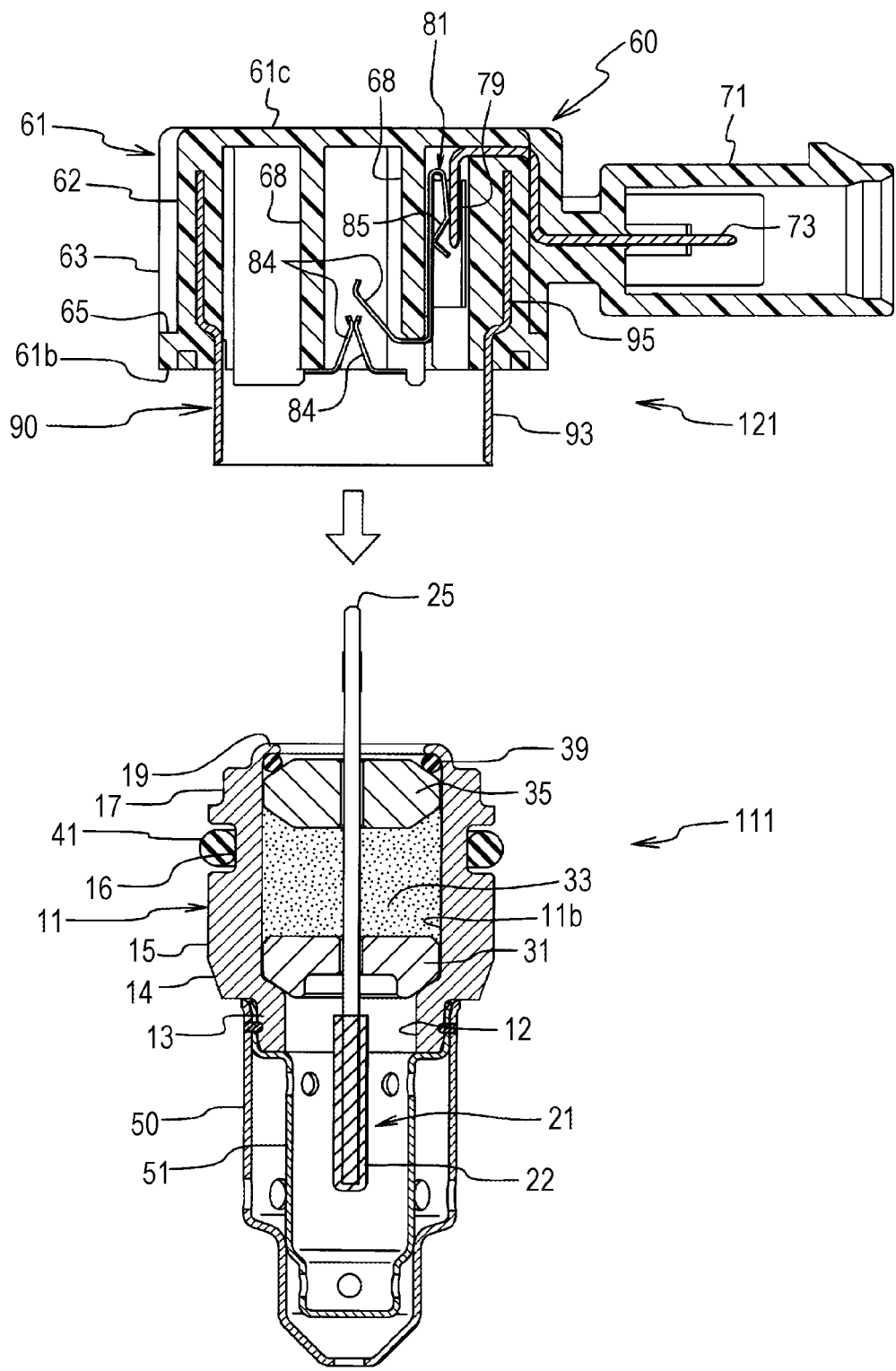
FIG. 6 illustrates a process of manufacturing and assembling the gas sensor of FIG. 1.
Figure 7A:
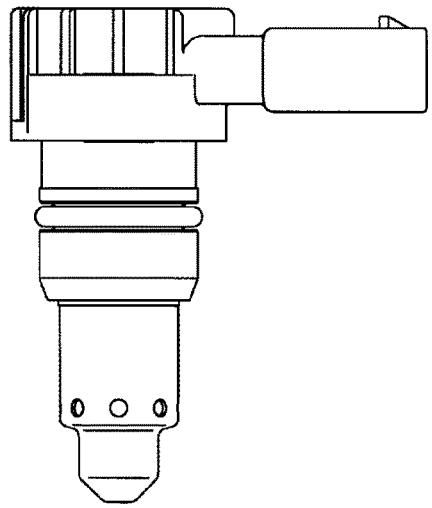
FIG. 7A is a front view.
Figure 7B:
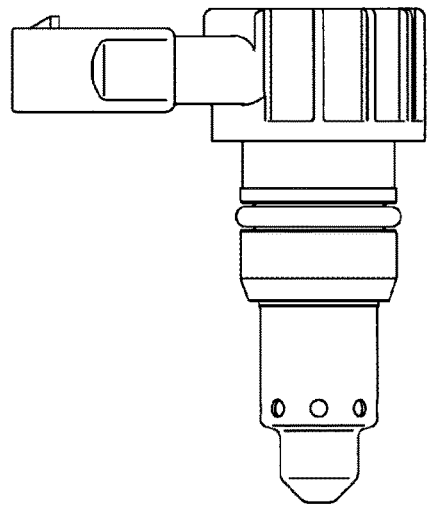
FIG. 7B is a rear view.
Figure 7C:
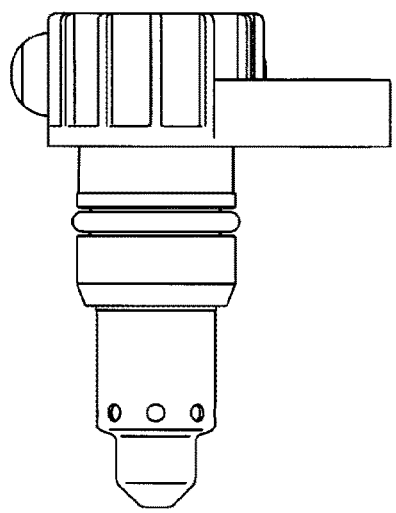
FIG. 7C is a left side view.
Figure 7D:
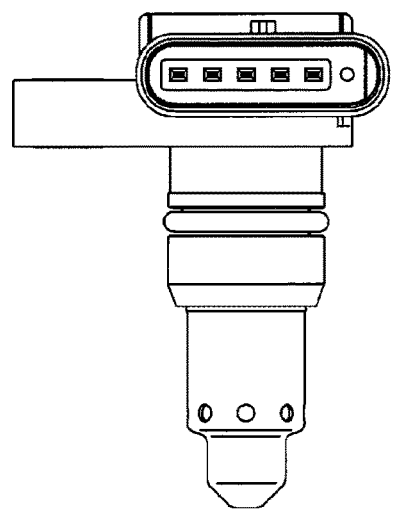
FIG. 7D is a right side view.
Figure 7E:
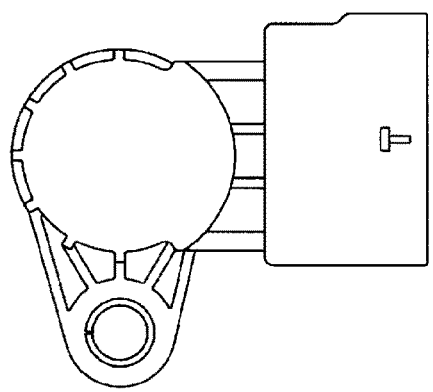
FIG. 7E is a plan view.
Figure 7F:
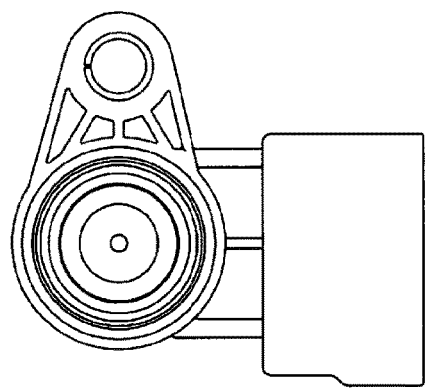
FIG. 7F is a bottom view, each illustrating the external shape of the gas sensor of FIG. 1.

As illustrated in FIG. 6, a semi-assembly 111 on the element 21 side, including the metal shell 11 to which the element 21 and the like are fixed, and a semi-assembly 121 on the protective cover 60 side, in which the metal terminals 81 are disposed in the accommodation spaces, are positioned relative to each other so that the metal shell 11 and the cylindrical cover portion 61 are disposed coaxial with each other. Then, the front end of the metal tube 90 of the protective cover 60 is fitted onto the protective-cover-fixing annular portion 17 adjacent to the rear end of the shell 11. Thus, a portion of the element 21 adjacent to the rear end 25, which protrudes rearward in the semi-assembly 111 shown in a lower part of FIG. 6, is inserted into a space between the metal terminals 81, which are disposed so as to face each other in the protective cover 60 of the semi-assembly 121 shown in an upper part of FIG. 6. When the element 21 is inserted in this way, electrode terminals disposed on a rear end portion of the element 21 and the metal terminals 81 accommodated in the cylindrical cover portion 61 are pressed against each other and electrically connected to each other through the first contact pieces 84 of the metal terminals 81. Then, the front end of the tube 90 is, for example, laser welded to the shell 11 in the circumferential direction. By doing so, the sensor 101 illustrated in FIG. 1 and other figures is obtained. The elastic sealing member 41 may be mounted on the shell 11 after the welding has been performed.

Figure 8:
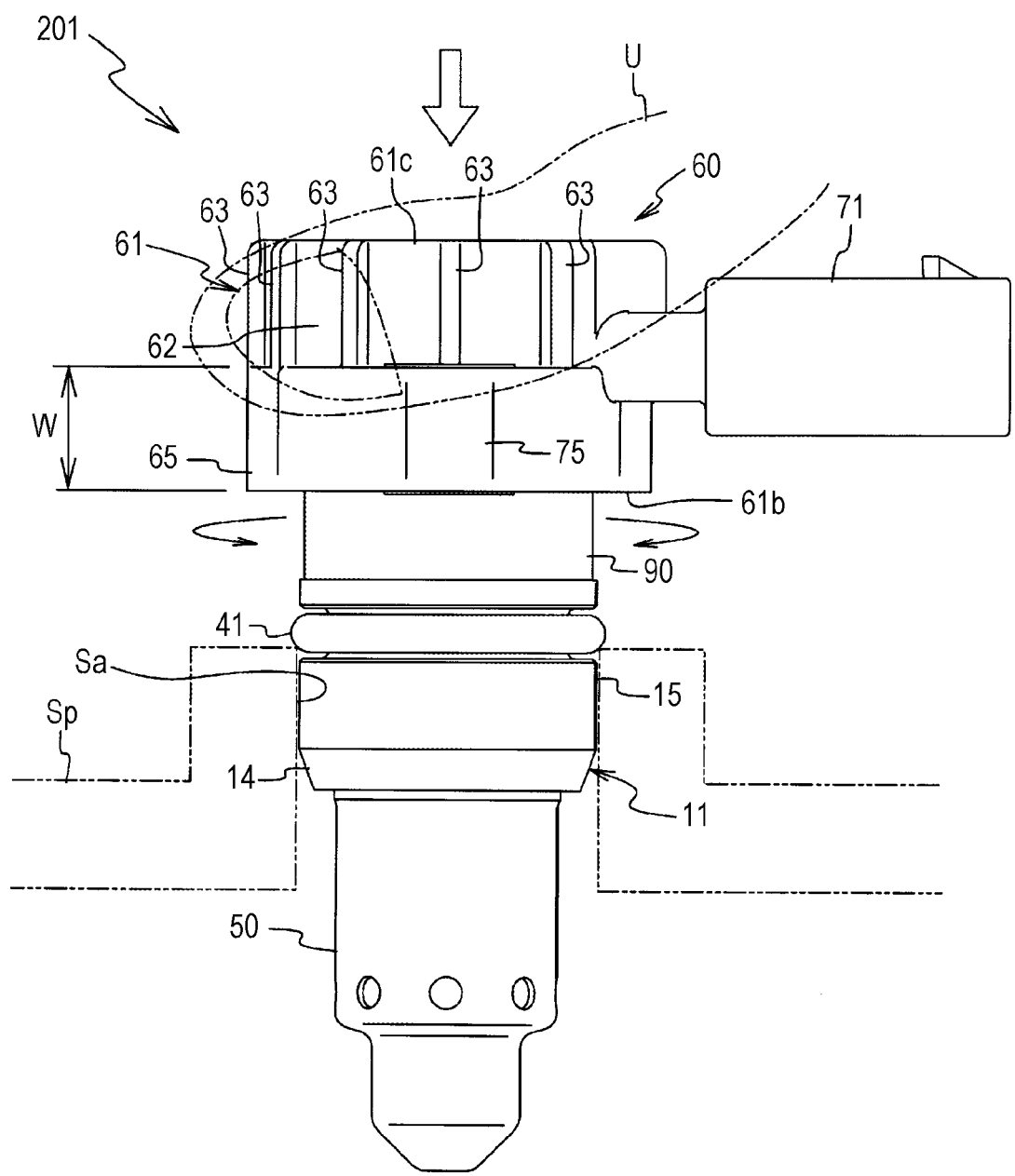
FIG. 8 illustrates a modification of the gas sensor of FIG. 1 when press-fitting the gas sensor into an attachment hole in an object.
Figure 9:
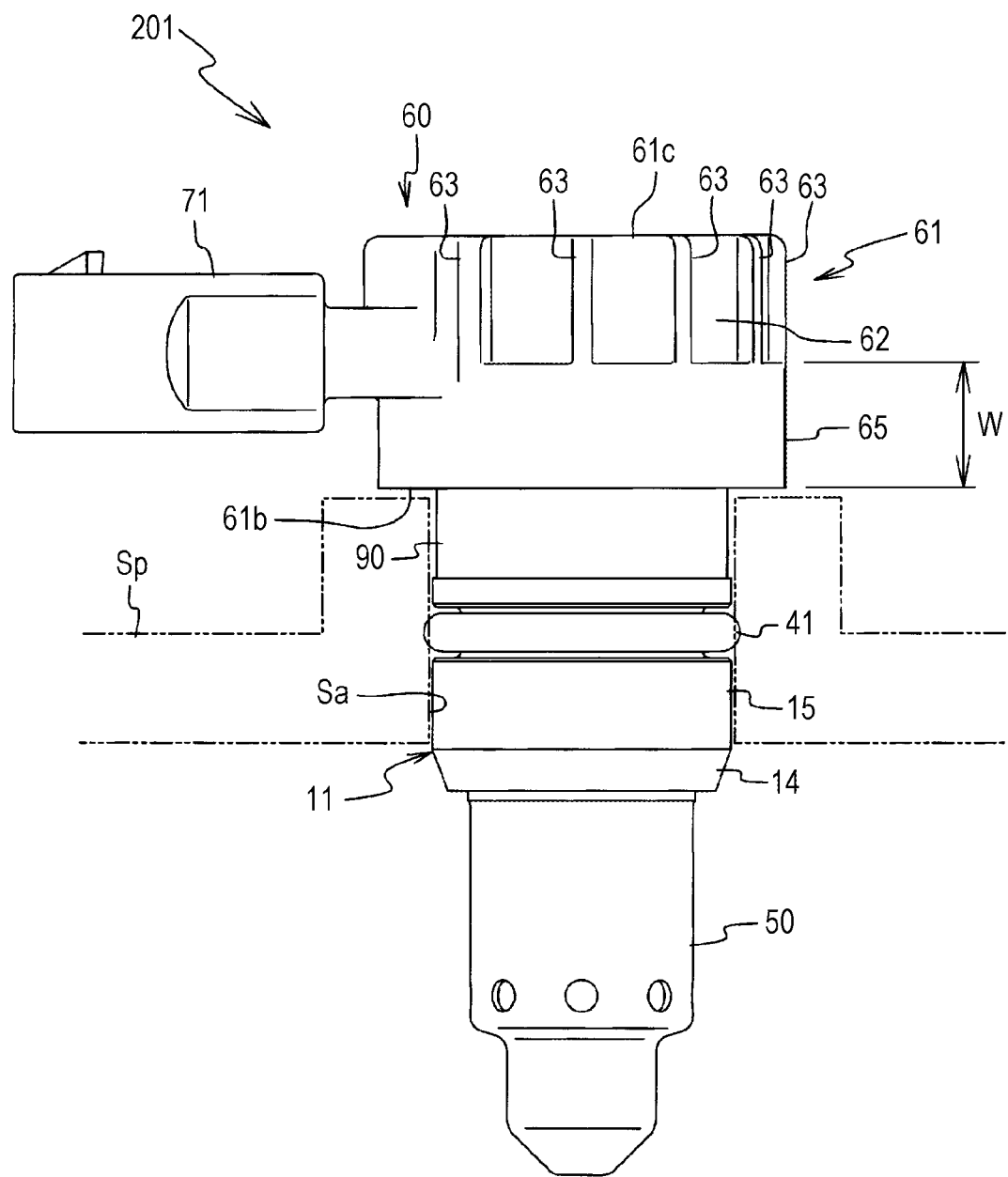
FIG. 9 is a rear view of the gas sensor of FIG. 8 after having been press-fitted into the attachment hole in the object.
Figure 10A:
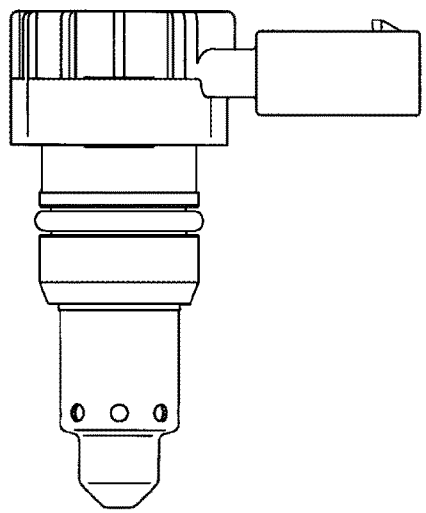
FIG. 10A is a front view.
Figure 10B:
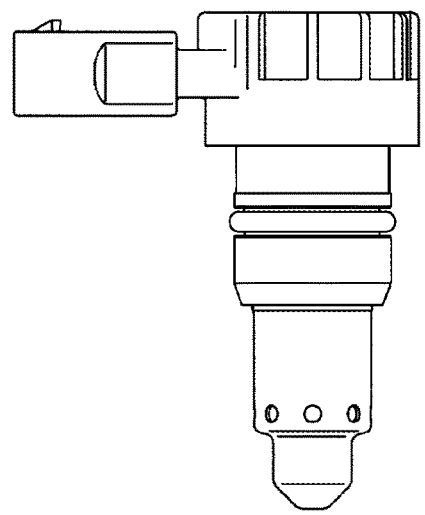
FIG. 10B is a rear view.
Figure 10C:
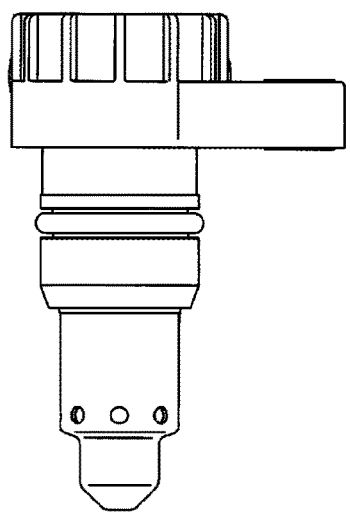
FIG. 10C is a left side view.
Figure 10D:
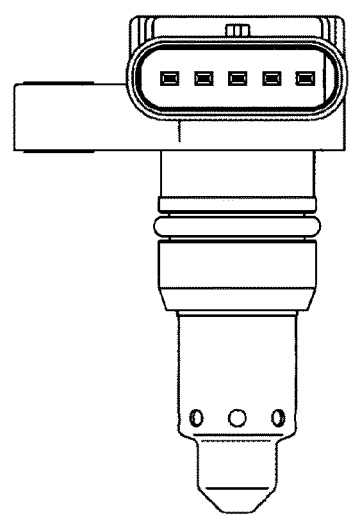
FIG. 10D is a right side view.
Figure 10E:
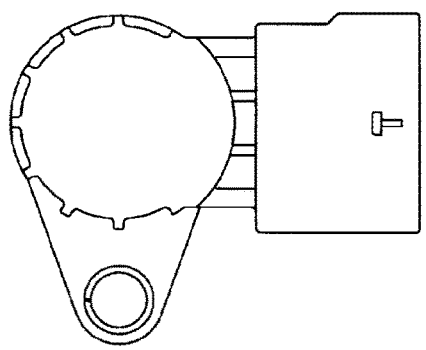
FIG. 10E is a plan view.
Figure 10F:
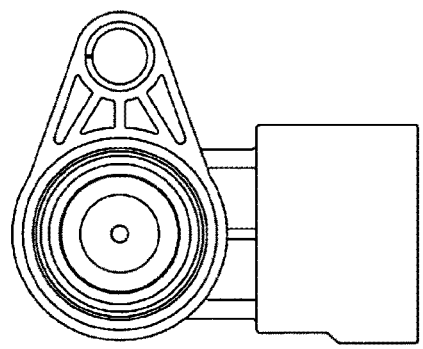
FIG. 10F is a bottom view, each illustrating the external shape of the gas sensor of FIG. 8.

Next, a gas sensor 201 according to a modification of the embodiment of the present invention will be described with reference to FIGS. 8 to 10. This modification does not essentially differ from the embodiment described above. Therefore, only the difference between the modification and the embodiment will be described. Elements of the modification that are the same as those of the embodiment will be denoted by the same numerals, and redundant descriptions will be omitted. The main difference is that the width W of the horizontal rib 65, which is disposed on the outer peripheral surface 62 of the cylindrical cover portion 61 of the protective cover 60, in the modification is larger than that of the embodiment described above. The width W is about a half of the height (the length in the front-rear direction) of the cylindrical cover portion 61. Therefore, in the modification, the lengths of the vertical ribs 63 in the front-rear direction are relatively small. However, because the cylindrical cover portion 61 has a sufficient height (length in the front-rear direction), this does not matter when an operator grips the cylindrical cover portion 61 when attaching the gas sensor 201. This modification is suitable for a case where the pressure of a gas to be measured is relatively high. This is because, since the width W of the horizontal rib 65 in the front-rear direction is larger than that of the embodiment described above, the cylindrical cover portion 61 and the tube 90 can be more tightly joined to each other, so that airtightness is increased. In this modification, the thickness (length in the front-rear direction) of the bracket 75 is the same as that of the embodiment.

A gas sensor according to the present invention is not limited to the embodiment and the modification described above, and the protective cover and the cylindrical cover portion of the gas sensor may be modified as appropriate. An object of the present invention is to solve the aforementioned problems, which may occur in a case where the cylindrical cover portion, which is to be gripped or held when attaching the gas sensor, is made of a resin. Therefore, it is not necessary that the entirety of the protective cover be made of a resin, and the protective cover may have a composite structure including a resin cylindrical cover portion. The resin material of the cylindrical cover portion may be selected from any polymer (resin) having an appropriate strength, heat resistance, and moldability. In the embodiment and the modification described above, the detection element has a strip-like shape having a rectangular cross section and extending in the front-rear direction. Alternatively, a detection element used in a gas sensor according to the present invention may have a square cross section or may have another cross-sectional shape. In the embodiment and the modification described above, the gas sensor is a wideband air-fuel ratio sensor. However, the present invention can be applied to any gas sensor, as long as the gas sensor can be press-fitted into and airtightly attached to an attachment hole by an operator by holding a resin cylindrical cover portion with his/her fingers and twisting the gas sensor.

What is claimed is:
1. A gas sensor to be airtightly attached to an attachment hole in an object, the gas sensor comprising:
   a metal shell;
   a ring-shaped elastic sealing member that provides airtight sealing in the attachment hole and is mounted on an outer peripheral surface of the metal shell;
   a detection element that is disposed in the metal shell;
   a metal terminal that is electrically connected to the detection element;
   a protective cover that is fixed to a rear end of the metal shell or a portion adjacent to the rear end of the metal shell so as to be unrotatable around an axis of the metal shell, the protective cover covering a rear end of the detection element and the metal terminal; and
   a metal tube that is embedded in the protective cover and is coaxially fixed to the metal shell, wherein
   the protective cover includes a resin cylindrical cover portion that has an axis that is substantially parallel to the axis of the metal shell, the cylindrical cover portion serving as a grip when attaching the gas sensor to the attachment hole,
   the cylindrical cover portion includes a plurality of vertical ribs on an outer peripheral surface thereof, the vertical ribs extending substantially parallel to the axis of the cylindrical cover portion so that protrusions and recesses are provided in a circumferential direction,
   the metal tube has a small-diameter portion in a front portion thereof and a large-diameter portion in a rear portion thereof, and
   the large-diameter portion of the metal tube is entirely embedded in the resin cylindrical cover portion of the protective cover.
2. The gas sensor according to claim 1, wherein,
   the protective cover is fixed to the portion adjacent to the rear end of the metal shell, said portion being provided at a front end of the tube or a portion adjacent to the front end of the tube, and the cylindrical cover portion includes a horizontal rib that extends in the circumferential direction and that bulges on a portion of the outer peripheral surface of the cylindrical cover portion surrounding the outer peripheral surface of the tube.

3. The gas sensor according to claim 2,
where the horizontal rib is provided at a front end of the cylindrical cover portion.

4. The gas sensor according to claim 1,
wherein the metal shell has an annular shape.

5. The gas sensor according to claim 1,
wherein the metal shell has a tubular shape.

6. The gas sensor according to claim 1,
wherein the axis of resin cylindrical cover portion is substantially concentric to the axis of the metal shell.

7. The gas sensor according to claim 1,
wherein an rear end of the large-diameter portion is positioned further rearward than the rear end of the detection element.

8. The gas sensor according to claim 1,
wherein the metal tube further includes a boundary portion between the small-diameter portion and the large-diameter portion, and
the boundary portion extends diagonally to the axis of the cylindrical cover portion.

9. The gas sensor according to claim 1, wherein all of outer surfaces of the large-diameter portions are directly abutted by the resin cylindrical cover portion of the protective cover.

* * * * *